US010617797B2

(12) United States Patent
Generalova et al.

(10) Patent No.: US 10,617,797 B2
(45) Date of Patent: Apr. 14, 2020

(54) COMPOSITE MATERIAL FOR THE X-RAY CONTRAST IMAGING OF NON-X-RAY CONTRAST IMPLANTS

(71) Applicant: LIMITED LIABILITY COMPANY "BIOSTEN" (BIOSTEN LLC.), "Skolkovo" Moscow (RU)

(72) Inventors: Alla Nikolaevna Generalova, Moscow (RU); Anna Igorevna Prostyakova, Moscow (RU); Igor Ivanovich Pashkin, Moscow (RU); Vitaly Pavlovich Zubov, Moscow (RU); Dmitry Valeryevich Kapustin, Moscow (RU)

(73) Assignee: LIMITED LIABILITY COMPANY "BIOSTEN", Moscow (RU)

( * ) Notice: Subject to any disclaimer, the term of this patent is extended or adjusted under 35 U.S.C. 154(b) by 78 days.

(21) Appl. No.: 15/739,949

(22) PCT Filed: Dec. 18, 2015

(86) PCT No.: PCT/RU2015/000896
§ 371 (c)(1),
(2) Date: Dec. 26, 2017

(87) PCT Pub. No.: WO2016/209107
PCT Pub. Date: Dec. 29, 2016

(65) Prior Publication Data
US 2018/0185554 A1     Jul. 5, 2018

(30) Foreign Application Priority Data
Jun. 26, 2015 (RU) .................. 2015125340

(51) Int. Cl.
| A61F 2/82 | (2013.01) |
| A61L 31/18 | (2006.01) |
| A61K 49/04 | (2006.01) |
| A61L 31/10 | (2006.01) |
| A61L 31/12 | (2006.01) |

(52) U.S. Cl.
CPC .............. *A61L 31/18* (2013.01); *A61K 49/04* (2013.01); *A61K 49/0409* (2013.01); *A61L 31/10* (2013.01); *A61L 31/125* (2013.01); *A61F 2/82* (2013.01)

(58) Field of Classification Search
CPC ...................................................... A61F 2/82
See application file for complete search history.

(56) References Cited

U.S. PATENT DOCUMENTS

| 6,355,058 | B1 | 3/2002 | Pacetti et al. | |
| 2007/0191708 | A1 | 8/2007 | Gerold et al. | |
| 2007/0207186 | A1* | 9/2007 | Scanlon ............ | A61F 2/07 424/424 |

FOREIGN PATENT DOCUMENTS

| RU | 2 173 173 | 9/2001 |
| RU | 2 173 173 C2 | 9/2001 |
| RU | 2 221 802 C1 | 1/2004 |
| WO | WO 01/49340 | 7/2001 |

OTHER PUBLICATIONS

International Search Report issued in Appln. No. PCT/RU2015/000896 dated Apr. 14, 2016.
International Preliminary Report on Patentability issued in PCT/RU2015/000896 dated Dec. 26, 2017.
Gollol Raju et al., "Contrast induced neurotoxicity following coronary angiogram with Iohexol in an end stage renal disease patient" *World J Clin Cases*, vol. 3, No. 11: 942-945 (2015).
Harvey et al., "The Influence of Contrast Medium Dose on Filtration Fraction in the Rabbit Kidney" *Investigative Radiology*, vol. 18: 441-444 (1983).
Hayward et al., "Contrast agents in angiocardiography" *Review: Br Heart J*, vol. 52: 361-368 (1984).
Hildreth et al., "Persistence of the 'Hydralazine Syndrome'" *J. Am. Med. Assoc.*, vol. 173, No. 6: 657-660 (Jun. 11, 1960).
Kartashov et al. "A new X-ray contrast agent for bronchography" New Medical Techniques for Medical and Social Rehabilitation, Yekaterinburg, pp. 93-96 (1995).
Kharuzhyk S.A., "Magnetic resonance imaging in medical practice" *Healthcare*, 8: 40-47 (2016) (w/ abstract).
Knoefel et al., "Sodium versus Meglumine Diatrizoate in Excretory Urography" *Investigative Radiology*, vol. 9, No. 5: 117-125 (1974).
Strekalov et al. "The Problem of Nephropathy Induced by Endocavitary Administration of Iodine-Containing X-ray Contrast Agents" *International Journal of Medical Imaging*, vol. 4, No. 3: 17-22 (2016).
Strekalov et al., "Prospects for Use of Iodine-free Radiopaques for Cholecystocholangiography" *Urals State Medical Academy: Institute for Chemistry of Solids*, Urals Branch, Russian Academy of Sciences, Central City Clinical Hospital One, Yekaterinburg, No. 1: 45-53 (2007).
Zuev et al., "New Radiopaque Contrast Agents based on RE Tantalates and Their Solid Solutions" *SOP Transactions on Physical Chemistry*, vol. 1, No. 2: 53-64 (2014).

(Continued)

*Primary Examiner* — Matthew W Schall
(74) *Attorney, Agent, or Firm* — Nixon & Vanderhye P.C.

(57) ABSTRACT

The invention relates to the field of biotechnology and medicine, more precisely, to manufacturing technique of implantable medical devices (stents) containing organic lanthanum compound-based X-ray contrast agents distributed within the coating.

The objective of this invention is the development of a biocompatible (and biodegradable) polymeric coating with glycolane on the surface of polymeric biodegradable vascular stents and other polymeric implants, which ensures, by means of introduction into a stent, satisfactory radiopacity both during stent installation in a patient and after installation, with a simultaneous additional positive effect provided by therapeutic properties of glycolane.

2 Claims, No Drawings

(56) References Cited

OTHER PUBLICATIONS

Zuev et al., "Radiopaque Contrast Agents Based on Bulk and Nanosized $La_{1-x}Gd_xTaO_4$ and $Gd_2O_3$" *Organic and Medicinal Chemistry International Journal*, vol. 4, iss. 2: 1-3 (2017).

* cited by examiner

COMPOSITE MATERIAL FOR THE X-RAY CONTRAST IMAGING OF NON-X-RAY CONTRAST IMPLANTS

This application is the U.S. national phase of International Application No. PCT/RU2015/000896 filed Dec. 18, 2015 which designated the U.S. and claims priority to Russian Patent Application No. 2015125340 filed Jun. 26, 2015, the entire contents of each of which are hereby incorporated by reference.

The invention relates to the field of biotechnology and medicine, more precisely, to implantable medical devices manufacturing technique, including vascular stents containing organic lanthanum compound-based X-ray contrast agents distributed within the coating.

An implant is an endoprosthesis (i.e., an artificial device implanted in the body to replace some part of an organ or a whole organ), or an identifier (e.g., a data chip implanted in the body), or implantable drug capsules or vascular stents intended for a lumen or blood vessel segment expansion (stents suitable for replacement of other anatomical pathways, such as urinary tract, biliary ducts, etc., are used in practice as well). Vascular stents are used for treatment of atherosclerotic stenosis of blood vessels (and as components of other organs).

During the first stage of implant installation, it is essential to assess the area which can be damaged during introduction and installation of the implant; to do so, a sufficient X-ray image of the installation area is required. In order to obtain the respective image for improved visualization, a contrast agent containing an X-ray contrast material, such as iodine or an iodine-containing substance, is normally introduced into the implant installation area in advance. The term "X-ray contrast" refers to the ability of a substance to absorb X-rays. The use of such substances for X-ray imaging (normally, a light background against a dark background) allows a physician to determine the area intended for a medicinal manipulation, as well as to monitor the position of a special-purpose catheter intended for implant delivery and precise installation in the required area. It is normally achieved using X-ray examination or similar procedures of X-ray imaging.

Vascular stents made of biodegradable polymers are a good example of such implants. Introduction of X-ray contrast materials into such stents or their coating enables direct visualization by X-ray imaging.

Stents made of biodegradable polymers are of particular interest as the time of their biodegradation can be chosen depending on the required service life of a stent; thus, the material of such stents ensures their complete biodegradation as soon as they are not clinically required any longer. Polymers and, more specifically, biodegradable polymers (which normally contain carbon, hydrogen, oxygen, and nitrogen) are non-radiopaque, which is a major drawback.

In order to eliminate this drawback, stents with a coating containing an X-ray contrast agent are being developed, which enables visualization of a stent by X-ray imaging. A coating made of biodegradable materials containing X-ray contrast agents is developed in some cases. A biodegradable X-ray contrast layer reacts with body fluids during delivery and installation of a stent. Thus, the X-ray contrast layer can be destroyed completely, together with the remaining stent. X-ray contrast agents which fail to degrade are eliminated from the body.

An X-ray contrast coating shall be resistant and able to maintain its properties during delivery and installation of a stent. Apart from that, the X-ray contrast coating shall not impair mechanical properties of a stent.

Water-soluble iodine compounds, such as acetotrizoate, diatrizoate, iodimide, ioglycate, iothalamate, ioxyphthalamate, selectan, uroselectan, diodon, metrizoate, metrizamid, iohexol, ioxaglat, iodixanol, lipidial, etiodol, and combinations thereof can be used as X-ray contrast agents.

Apart from halogen-containing compounds, typical metals which can be used as X-ray contrast agents include iron, magnesium, zinc, platinum, gold, and tungsten. Moreover, oxides of these and other metals can be used as X-ray contrast agents. Metals degrading under environmental conditions can be used as well, provided that the metal dissolution products have no negative impact on a patient's body. Magnesium, zinc, tungsten, and iron are typical degradable metals.

Typical biocompatible metal salts which can be used for an X-ray contrast coating include iron sulfate, iron gluconate, iron carbonate, iron chloride, iron fumarate, iron iodide, iron lactate, iron succinate, barium sulfate, bismuth hydrocarbonate, bismuth tartrate or sodium tartrate, potassium iodide, bismuth salicylate, zinc acetate, zinc carbonate, zinc citrate, zinc iodate, zinc iodide, zinc lactate, zinc phosphate, zinc salicylate, zinc stearate, zinc sulfate, some other compounds and combinations thereof.

A comprehensive review of medical application of X-ray contrast agents is provided in the thesis paper by I. M. Strekalov [I. M. Strekalov. A new X-ray contrast compound, lanthanum orthotantalate, and its possible use in abdominal surgery. Ph.D. thesis in Medical Science, Chelyabinsk, 2007, 120 p.]. In particular, the paper states that parenteral agents, mostly iodine-containing X-ray contrast agents, form the largest group of such agents. Iodine-containing X-ray contrast agents shall ensure high contrast and shall demonstrate pharmacological and physiological inactivity, as well as low toxicity. These substances shall ensure uniform adsorption on mucosal surfaces of organs and cavity walls as a thin layer, without accumulation in small-diameter lumens and obstruction thereof. They shall be promptly eliminated from the body and, finally, shall have a sufficiently low cost. The use of oil-based and water-soluble iodine- and barium-containing X-ray contrast agents has a number of drawbacks; in particular, it does not enable complete assessment of the hepatic tree lumen and ducts of other organs as uniform clear contrasting using the agents mentioned above is not always possible for a number of reasons, such as mechanical mucosal irritation [G. L. Vol-Epstein, L. S. Tapilsky. Experience in application of oil-based contrast agents//Chest Surg. 1978.—No. 1.—P. 90-95]; barium sulfate agents are high-contrast, but are eliminated from ducts slowly, their particles stick together in a lumen, causing obstruction, which leads to development of cholangitis, reactive hepatitis, and pancreatitis [G. L. Feofilov Selected chapters of bronchography.—Moscow: Medicine, 1971.—181 p.; T. Johnson, W. Howland, P. Redgan. The examination of digestive tract with new modification of Barium sulfats//Sth. Med. J. (Bgham. Ala.). 1971.—Vol. 64.—P. 1024]. Parenteral water-soluble iodine-containing X-ray contrast agents (Urografin, Trazograph, Omnipaque, Ultravist, etc.) have gained widespread use, along with oil-soluble X-ray contrast agents. Many agents of this group are also used for intracavitary administration. At that, side effects are the same as those observed in intravascular administration. This is due to the ability of X-ray contrast agents to absorb into the blood stream of the small intestine during contrasting of gastrointestinal organs and hepatobiliary system. They are known to have toxic effect on blood, kidneys, liver, central nervous system, and, in particular, on thyroid gland [I. Kh. Rabkin. Prevention of complications in lymphangiography//Angiography. Moscow.—1977.—P. 5-11; L. S. Rosenshtraukh. Prevention of complications in X-ray examination using contrast agents//Bulletin of Roentgenology and Radiology. 1978.—No. 9.—P. 31-35; N. K. Sviridov, P. V. Sergeev. Neurotoxicity of X-ray contrast agents//Pharmacology and Toxicology. 1979.—No. 4.—P. 435-442; P. Knoefel, R. Kraft, R. Knight, S. Moore. Sodium versus meglumine diatrizoate in excretory urography//Invest. Radiol. 1974.—Vol. 9, No. 5.—P. 117-125; L. A. Harvey, W. J. H. Caldicott. The influence of contrast medium dose on filtration fraction in the rabbit kidney// Invest. Radiol. 1983.—Vol. 18.—P. 441-444]. According to clinical trials, a positive test reaction has a weak correlation with allergic reactions, thus, its value in forecasting of a fatal outcome or severe reactions to administration of a diagnostic X-ray contrast agent dose is doubtful, and complications can be observed in patients with negative tests [E. A. Hildreth, C. E. Biro, T. A. McCreary. Persistence of the hydralazine syndrome//J. Am. Med. Assoc. 1960.—Vol. 173.—P. 657; Ansel G. Adverse reactions to contrast agents//Ivest. Radiol., 1970.—Vol.—P. 374-384]. Apart from that, introduction of iodine-containing X-ray contrast agents into hepatic and pancreatic duct system often leads to development of cholangitis and acute pancreatitis (up to pancreonecrosis).

Development of this section of pharmacology includes the following main directions: improvement of triiodide-containing X-ray contrast agents, in particular, of non-ionic triiodide-containing X-ray contrast agents subgroup [I. S. Amosov, R. G. Nikitina, G. V. Menzhinskaya. Challenges of development and application of X-ray contrast agents in oncology. Moscow.—1985.—124 p.; N. K. Sviridov, Zh. V. Sheikh. Magnetic resonance imaging in medical practice// Bulletin of Roentgenology and Radiology. 1997.—No. 2.—P. 5.], search for new vehicles for iodine-containing X-ray contrast agents ensuring selective accumulation of X-ray contrast agents in organs (liposomes, micellae); synthesis of metal-based X-ray contrast agents; development of X-ray contrast agents capable of controlled accumulation in organs and systems of the body (ferromagnetic X-ray contrast agents); combining of various classes of X-ray contrast agents; the use of various additives enabling decrease in the dose of a combined X-ray contrast agent (e.g., for a bio-contrast examination) and improving organoleptic properties (for parenteral X-ray contrast agents). Currently, the main direction of X-ray contrast agents improvement is the development of new iodine-containing agents, as well as improvement of organoleptic properties of barium sulfate agents, such as development of non-ionic triiodide-containing X-ray contrast agents with lower toxicity, as compared with ionic mono- and diiodide-containing agents. At the same time, the search for agents containing other elements of the periodic table with high density and low toxicity is in progress.

The rare earth group, in particular, tantalum, lanthanum, yttrium, niobium, and hafnium, is of great interest to researches [P. V. Sergeev, N. K. Sviridov, N. L. Shimanovsky. Contrast agents. Moscow: Medicine.—1993.— 254 p.; M. G. Zuyev, L. P. Larionov. Rare earth compounds with monoatomic and polyatomic anions of group V transition metals/Institute of Chemistry of Solids of the Ural Branch of the Russian Academy of Sciences.—Yekaterinburg. 1999.—282 p.] et al. Yttrium orthotantalate is an X-ray contrast agent of tantalate group which has already been described and preclinically evaluated [V. M. Kartashov, M. G. Zuyev, A. F. Dmitriev, A. A. Fotiyev. A new X-ray contrast agent for bronchography//New Medical Techniques for Medical and Social Rehabilitation.—Yekaterinburg. 1995.—P. 93-96; M. G. Zuyev, E. Yu. Zhuravleva, L. P. Larionov, V. A. Sokolov. X-ray contrast agents: composite oxides of group III-V elements (yttrium orthotantalate)/Ural State Medical Academy, Institute of Chemistry of Solids of the Ural Branch of the Russian Academy of Sciences.— Yekaterinburg. 1997.—74 p.]. This agent has shown high contrast properties during its in vitro comparison with barium sulfate, trazograph, and urografin, as well as in vitro during bronchography with a powdered form of the agent.

The main challenge in the use of non-water-soluble X-ray contrast agents as suspensions is that water suspension of these agents is an extremely unstable system; complete subsidence of the suspension only takes a few minutes, even for highly-dispersive agents. Insufficient X-ray diagnostic value has also been observed, which is due to incomplete filling of small cavities with X-ray contrast agents and, thus, impossibility to obtain a comprehensive X-ray image of the hepatic tree, unreliability of occlusive process diagnostics, high risk of inflammatory and purulent-septic complications of cholangitis, hepatitis, pancreatitis, pancreonecrosis, and cholangiogenic sepsis (in case of cholangiography). The use of a liquid gel form of lanthanum ortholanthanate, specially adapted for contrasting of bile ducts and gastrointestinal tract, has been proposed as a possible solution. At that, the benefits of radiopacity of the chemical compound based on the periodic table group III and V heavy elements (lanthanum and tantalum), as compared with iodine-containing X-ray contrast agents and the standard water suspension of barium sulfate, have been justified, and the respective agents suitable for X-ray contrast examinations, as well as for gastrointestinal organs and bile duct surgery, have been obtained.

Thus, the above-mentioned substances are widely used in medicine as X-ray contrast agents.

Apart from X-ray contrast agents suitable for direct administration, for example, as a suspension, several methods of X-ray contrast agent introduction into implants have been developed, which can be grouped as follows.

1. An X-ray contrast agent can be applied to an implant using such methods as spraying or dipping. Spraying or dipping procedures can be repeated several times to ensure the desired amount of an X-ray contrast agent on an implant. In other cases, a powdered X-ray contrast agent can be applied. The surface of an implant (stent) shall be moistened with a suitable solution in advance, after which a powdered X-ray contrast agent is applied to a wet implant surface. Moistening and application of a powder on a wet surface by means of its adhesion can be repeated several times to ensure the desired amount of a contrast agent on the surface of an implant.

An X-ray contrast coating shall contain a sufficient amount of an X-ray contrast agent to ensure visualization of an implant during the selected period of time after implantation. With regard to a stent, this period of time can vary from 10 minutes to 2 weeks; however, the possibility to locate a stent during a longer period after implantation is preferable as problems requiring reinstallation of a stent may arise.

2. An X-ray contrast coating, mostly consisting of an X-ray contrast agent, can dissolve quicker than necessary. In this case, a coating of non-water-soluble biodegradable polymer with a dispersed X-ray contrast agent is developed. Typical examples of such polymers include poly-(L)-lactide), poly-(D,L)-lactide), polyglycolic acid, polycaprolactone, and their copolymers. Radiopacity of a coating can be adjusted by changing the X-ray contrast agent concentration and the thickness of biodegradable polymer layer with an X-ray contrast agent. A biodegradable polymer in an X-ray contrast coating can be the same or different from the stent material. The required stent degradation time is normally different from stent visualization time; in most cases, degradation requires more time. Thus, in some cases, a biodegradable polymer in an X-ray contrast coating can have a higher degradation rate.

3. An X-ray contrast agent can be dispersed in a water-soluble polymer from which an X-ray contrast coating is made. X-ray contrast coatings made of water-soluble polymers normally have a shorter service life, as compared with those made of a non-water-soluble hydrolytic ally degradable polymer.

4. An X-ray contrast agent can be introduced into a block copolymer consisting of non-water-soluble blocks, which degrade due to hydrolysis, and water-soluble blocks. Thus, the service life of an X-ray contrast coating can be controlled by adjusting the content of water-soluble and non-water-soluble blocks. The increase in content of water-soluble blocks increases the degradation rate and decreases the service life of an X-ray contrast coating.

5. A stent can have a polymer layer above an X-ray contrast coating. The top layer can increase the service life of an X-ray contrast coating by means of decrease or prevention of water absorption, i.e., the top layer acts as a protective screen. Water-soluble polymers, non-water-soluble hydrolytically degradable polymers, or block copolymers can be used as a top layer as well.

6. In addition to an X-ray contrast coating, a coating of a drug encapsulated into a polymer solution can be created on a stent. The layer containing a drug and a polymer can include a therapeutic agent or a drug mixed with a biodegradable polymer or dispersed in a biodegradable polymer. This layer can increase the service life of an X-ray contrast coating and can ensure the delivery of a drug to a vessel lumen. Water-soluble polymers, non-water-soluble hydrolytically degradable polymers, or block copolymers can be used as a base for the drug-containing layer.

The closest analogous technical solution for the claimed solution is a composite material for imaging of non-radiopaque implants, containing particles of an X-ray contrast agent selected from a group of materials, including gold, platinum, iridium, tantalum, silver, molybdenum, iodine, and salts of the said compounds, as well as bismuth and its salts, stanum, rhenium, osmium, and palladium, distributed in a coupling polymeric medium (WO 2001049340).

The drawbacks of this solution are that the material contains allergens and is not biodegradable, and X-ray contrast agents contained in the material can remain in the body for years. In certain cases, application of such materials is limited by allergic reactions they cause in patients.

The objective of this invention is the development of a composite material for imaging of non-radiopaque implants, which is hypoallergenic and easily removable from a patient's body.

The technical result is the controlled release of an X-ray contrast agent from an implant and its elimination from the body, with reduced side effects, including allergic reactions.

This task can be solved, and the technical result can be obtained by development and use of the composite material option. A composite material for imaging of non-radiopaque implants has been developed based on the first version of the invention, which contains a base and an X-ray contrast agent and is different in that it contains 32.5-59 mass percent of glycolane as the X-ray contrast agent, as well as polyvinyl alcohol and chitosan in the ratio of 25:1 as the base. A composite material for imaging of non-radiopaque implants has been developed based on the second version of the invention, which contains a base and an X-ray contrast agent and is different in that it contains 79-88 mass percent of glycolane as the X-ray contrast agent, as well as polylactic acid microspheres as the base.

An organic lanthanum compound, glycolane, is used as an X-ray contrast agent in this invention. Glycolane (triethylene glycol trinitrate lanthanum monohydrate) is a complex compound of lanthanum nitrate and triethylene glycol. Lanthanum is one of rare earth metals, lanthanoids. Some lanthanoids, including lanthanum, were detected in human body. A small amount of them was detected in the spleen, and extremely small amounts (0.1 mg/kg) in dental tissue and enamel. Few data available do not indicate that lanthanoids are required for normal functioning of the body, but their ability to affect biological processes is beyond any doubt. As good complex formers, they can complex with many organic ligands (carbohydrates, amino acids, oxy acids, nucleotides, phosphatides, vitamins) Glycolane is known to have antimicrobial activity and efficient anticoagulant properties. Lanthanoids affect various stages of blood coagulation process: they inhibit prothrombin synthesis, have antagonist properties with regard to thrombin, act as $Ca^{2+}$ metabolic antagonist and remove it from systems with one or several protein coagulation factors; they increase free heparin level in blood through mast cells in case of administration of sufficiently high doses. The effect of lanthanoids on biological functions is determined, in particular, by their ability to replace $Ca^{2+}$ in biological systems. Biological properties of lanthanoids are somewhat affected by the presence of f-electrons in electron shells of their atoms, which creates micro magnetic field effect. This explains the ability of lanthanoids to increase phagocytic activity of white blood cells. Lanthanum ions are also known for their inflammatory effect due to high affinity to phospholipids and ability to stabilize cell membranes by ion channel blocking; this effect of lanthanoids on a site of inflammation is similar to that of corticosteroids.

Thus, the use of lanthanum-containing compounds as X-ray contrast agents, in particular, in vascular stents, enables imaging of a stent both during its installation (at that, the use of delivery means with radiopaque markers is no longer required) and the subsequent period, as well as provides additional benefit, as compared with the existing solutions, by means of useful therapeutic properties of glycolane (first of all, by means of its anticoagulant effect).

The use of glycolane ensures controlled release of X-ray contrast agents (with a preset time interval) with immobilization of X-ray contrast agents in a biodegradable polymer layer (such as polylactic acid).

The use of glycolane as an X-ray contrast agent ensures satisfactory radiopacity by means of its introduction into a stent, both during stent installation in a patient and after installation, with a simultaneous additional positive effect provided by therapeutic properties of glycolane. The use of organic lanthanum compound, in contrast to its inorganic salts, enables more uniform distribution of an X-ray contrast agent particles in the polymeric matrix (in particular, when making an implant coating).

Thus, the particular features mentioned above are indissolubly connected, which ensures the causal relationship with the technical result achieved by combining of the said features.

The invention can be illustrated by the following examples.

EXAMPLE 1

In order to obtain an X-ray contrast surface coating of a stent made of polylactic acid or polylactic acid copolymer with glycolide, disperse 50 mg of glycolane in 1 ml of 10% water solution of polyvinyl alcohol (PVA, MW 10000) in a 1.5-ml microcentrifuge plastic tube. In order to decrease solubility of PVA film in water, add 400 µl of 1% chitosan solution in mixture of 1% acetic acid and ethanol (1:1) to the PVA solution. Mix thoroughly, place in an ultrasonic bath for 1 minute, then mix again in a shaker for 1 hour at room temperature.

Put the stent blank intended for coating on a fluoroplastic rod with the diameter 0.05 mm smaller than that of the blank. Place the resulting structure in a 1.5-ml microcentrifuge tube and match the vertical axial line of the rod with the central vertical axis of the tube. Then, fill the tube with freshly-prepared ethanol to cover the top stratum of the blank. Place the system in the ultrasonic bath and sonicate (30-35 kHz) for 10 minutes at 40° C. Then incubate the system for 20 minutes at 40° C. Remove ethanol from the tube and fill it with the X-ray contrast agent-containing mixture to cover the top stratum of the blank. Then, incubate the system for 40 minutes at 25±1° C. Remove the rod with the blank from the tube and place vertically into a dryer to ensure uniform air blowing of the whole surface of the stent blank. Blanks shall be dried at 35±1° C. to dry weight.

The thickness of the resulting coating measured by probe microscopy is 120±10 nm.

EXAMPLE 2

In order to obtain an X-ray contrast surface coating of a stent made of polylactic acid or polylactic acid copolymer with glycolide, disperse 35 mg of glycolane in 1 ml of 10% water solution of polyvinyl alcohol (PVA, MW 10000) in a 1.5-ml microcentrifuge plastic tube. In order to decrease solubility of PVA film in water, add 200 µl of 1% chitosan solution in mixture of 1% acetic acid and ethanol (1:1) to the PVA solution. Mix thoroughly, place in an ultrasonic bath for 1 minute, then mix again in a shaker for 1 hour at room temperature.

Put the stent blank intended for coating on a fluoroplastic rod with the diameter 0.05 mm smaller than that of the blank. Place the resulting structure in a 1.5-ml microcentrifuge tube and match the vertical axial line of the rod with the central vertical axis of the tube. Then, fill the tube with freshly-prepared ethanol to cover the top stratum of the blank. Place the system in the ultrasonic bath and sonicate (30-35 kHz) for 10 minutes at 40° C. Then incubate the system for 20 minutes at 40° C. Remove ethanol from the tube and fill it with the X-ray contrast agent-containing mixture to cover the top stratum of the blank. Then, incubate the system for 40 minutes at 25±1° C. Remove the rod with the blank from the tube and place vertically into a dryer to ensure uniform air blowing of the whole surface of the stent blank. Blanks shall be dried at 35±1° C. to dry weight.

The thickness of the resulting coating measured by probe microscopy is 120±5 nm.

EXAMPLE 3

Increase glycolane content in the coating in order to improve radiopacity. To do so, disperse 15 mg of glycolane in 1 ml of 1% water solution of polyvinyl alcohol (PVA, MW 10000) in a 1.5-ml plastic tube. In order to decrease solubility of PVA film in water, add 40 µl of 1% chitosan solution in mixture of 1% acetic acid and ethanol (1:1) to the PVA solution. Mix thoroughly, place in an ultrasonic bath for 1 minute, then mix again in a shaker for 1 hour at room temperature.

Put the stent blank intended for coating on a fluoroplastic rod with the diameter 0.05 mm smaller than that of the blank. Place the resulting structure in a 1.5-ml microcentrifuge tube and match the vertical axial line of the rod with the central vertical axis of the tube. Then, fill the tube with freshly-prepared ethanol to cover the top stratum of the blank. Place the system in the ultrasonic bath and sonicate (30-35 kHz) for 10 minutes at 40° C. Then incubate the system for 20 minutes at 40° C. Remove ethanol from the tube and fill it with the X-ray contrast agent-containing mixture to cover the top stratum of the blank. Then, incubate the system for 40 minutes at 25±1° C. Remove the rod with the blank from the tube and place vertically into a dryer to ensure uniform air blowing of the whole surface of the stent blank. Blanks shall be dried at 35±1° C. to dry weight.

The thickness of the resulting coating measured by probe microscopy is 100±10 nm.

EXAMPLE 4

In order to obtain an X-ray contrast coating based on polymeric microspheres containing an X-ray contrast agent introduced by means of the X-ray contrast agent diffusion into preformed polymeric microspheres, prepare the said polylactic acid microspheres by adding 100 µl of polylactic acid solution in chloroform (20 mg/ml) in 5-µl batches, while mixing constantly in 1 ml of distilled water. Then, let the particle dispersion stand for 1 hour at 56° C. until the solvent evaporates completely. Purify the dispersion by centrifugation, by adding a tree-fold amount of water and removing the supernatant.

Add 50 µl of ethanol to 200 µl of the resulting polylactic acid particle dispersion and let the mixture stand for 1 hour, while mixing. Then, add 100 µl of glycolane water dispersion (15 mg/ml) at room temperature, mix thoroughly, and sonicate for 1 hour. Remove the excessive X-ray contrast agent from the particle dispersion by centrifugation.

Average size of the resulting polymeric particles containing the X-ray contrast agent, measured by laser correlation spectroscopy, was 410±10 nm.

Put the stent blank intended for coating on a fluoroplastic rod with the diameter 0.05 mm smaller than that of the blank. Place the resulting structure in a 1.5-ml microcentrifuge tube and match the vertical axial line of the rod with the central vertical axis of the tube. Then, fill the tube with freshly-prepared ethanol to cover the top stratum of the blank. Place the system in the ultrasonic bath and sonicate (30-35 kHz) for 10 minutes at 40° C. Then incubate the system for 20 minutes at 40° C. Remove ethanol from the tube and fill it with the X-ray contrast agent-containing mixture to cover the top stratum of the blank. Then, incubate the system for 40 minutes at 25±1° C. Remove the rod with the blank from the tube and place vertically into a dryer to ensure uniform air blowing of the whole surface of the stent blank. Blanks shall be dried at 35±1° C. to dry weight.

The thickness of the resulting coating measured by probe microscopy is 140±10 nm.

EXAMPLE 5

In order to obtain an X-ray contrast coating based on polymeric microspheres containing an X-ray contrast agent introduced by means of the X-ray contrast agent diffusion into preformed polymeric microspheres, prepare the said polylactic acid microspheres by adding 100 µl of polylactic acid solution in chloroform (20 mg/ml) in 5-µl batches, while mixing constantly in 1 ml of distilled water. Then, let the particle dispersion stand for 1 hour at 56° C. until the solvent evaporates completely. Purify the dispersion by centrifugation, by adding a tree-fold amount of water and removing the supernatant.

Add 50 µl of ethanol to 200 µl of the resulting polylactic acid particle dispersion and let the mixture stand for 1 hour, while mixing. Then, add 100 µl of glycolane water dispersion (20 mg/ml) at room temperature, mix thoroughly, and sonicate for 1 hour. Remove the excessive X-ray contrast agent from the particle dispersion by centrifugation.

Average size of the resulting polymeric particles containing the X-ray contrast agent, measured by laser correlation spectroscopy, was 405±10 nm.

Put the stent blank intended for coating on a fluoroplastic rod with the diameter 0.05 mm smaller than that of the blank. Place the resulting structure in a 1.5-ml microcentrifuge tube and match the vertical axial line of the rod with the central vertical axis of the tube. Then, fill the tube with freshly-prepared ethanol to cover the top stratum of the blank. Place the system in the ultrasonic bath and sonicate (30-35 kHz) for 10 minutes at 40° C. Then incubate the system for 20 minutes at 40° C. Remove ethanol from the tube and fill it with the X-ray contrast agent-containing mixture to cover the top stratum of the blank. Then, incubate the system for 40 minutes at 25±1° C. Remove the rod with the blank from the tube and place vertically into a dryer to ensure uniform air blowing of the whole surface of the stent blank. Blanks shall be dried at 35±1° C. to dry weight.

The thickness of the resulting coating measured by probe microscopy is 140±10 nm.

EXAMPLE 6

In order to obtain an X-ray contrast coating based on polymeric microspheres containing an X-ray contrast agent introduced during preparation of water emulsion of the polymer, quickly add 100 µl of polylactic acid (20 mg/ml) to 1 ml of water dispersion of glycolane (15 mg/ml), while mixing constantly and sonicating. Let the polylactic acid dispersion with glycolane stand for 1 hour at 56° C. until the solvent evaporates completely. Then, purify the dispersion by centrifugation.

Average size of the resulting polymeric particles containing the X-ray contrast agent, measured by laser correlation spectroscopy, was 180 nm.

Put the stent blank intended for coating on a fluoroplastic rod with the diameter 0.05 mm smaller than that of the blank. Place the resulting structure in a 1.5-ml microcentrifuge tube and match the vertical axial line of the rod with the central vertical axis of the tube. Then, fill the tube with freshly-prepared ethanol to cover the top stratum of the blank. Place the system in the ultrasonic bath and sonicate (30-35 kHz) for 10 minutes at 40° C. Then incubate the system for 20 minutes at 40° C. Remove ethanol from the tube and fill it with the X-ray contrast agent-containing mixture to cover the top stratum of the blank. Then, incubate the system for 40 minutes at 25±1° C. Remove the rod with the blank from the tube and place vertically into a dryer to ensure uniform air blowing of the whole surface of the stent blank. Blanks shall be dried at 35±1° C. to dry weight.

The thickness of the resulting coating measured by probe microscopy is 110±10 nm.

The invention claimed is:

1. A composite material for imaging of non-radiopaque implants comprising a base and an X-ray contrast agent, wherein the composite material comprises
    32.5-59 mass percent of glycolane as the X-ray contrast agent, as well as and
    polyvinyl alcohol and chitosan in a ratio of 25:1 of polyvinyl alcohol:chitosan as the base.

2. A composite material for imaging of non-radiopaque implants comprising a base and an X-ray contrast agent, wherein the composite material comprises
    79-88 mass percent of glycolane as the X-ray contrast agent and
    polylactic acid microspheres as the base.

* * * * *